US009974584B2

(12) United States Patent
Hashmi et al.

(10) Patent No.: US 9,974,584 B2
(45) Date of Patent: May 22, 2018

(54) LOCKING WEB PLATE

(71) Applicant: DePuy Synthes Products, Inc., Raynham, MA (US)

(72) Inventors: Adam Hashmi, West Chester, PA (US); Mirco Rocci, Zuchwil (CH); Lynn Kelly, West Chester, PA (US); Fabienne Fischer, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days. days.

(21) Appl. No.: 15/711,545

(22) Filed: Sep. 21, 2017

(65) Prior Publication Data

US 2018/0008327 A1    Jan. 11, 2018

Related U.S. Application Data

(63) Continuation of application No. 14/320,511, filed on Jun. 30, 2014, now Pat. No. 9,795,425.

(51) Int. Cl.
*A61B 17/88* (2006.01)
*A61B 17/80* (2006.01)

(52) U.S. Cl.
CPC .............................. *A61B 17/8061* (2013.01)

(58) Field of Classification Search
None
See application file for complete search history.

(56) References Cited

U.S. PATENT DOCUMENTS

| 2007/0239163 A1 | 10/2007 | Strnad et al. |
| 2010/0069966 A1 | 3/2010 | Castaneda et al. |
| 2011/0092981 A1 | 4/2011 | Ng et al. |
| 2012/0265254 A1 | 10/2012 | Horan et al. |
| 2013/0006311 A1 | 1/2013 | Castaneda et al. |
| 2014/0107798 A1 | 4/2014 | Jeng et al. |

FOREIGN PATENT DOCUMENTS

| DE | 202008012448 | 4/2010 |
| EP | 2623059 | 8/2013 |

OTHER PUBLICATIONS

Product Information: APTUS Wrist, Adaptive Distal Radious System2.5, Medartis, Switzerland, 2011, 24 sheets.

*Primary Examiner* — Sameh Boles
(74) *Attorney, Agent, or Firm* — Fay Kaplun & Marcin, LLP

(57) ABSTRACT

A bone plate for fixation to a phalanx includes a head extending from a first end to a second end and having first and second fixation element holes extending therethrough, a connection portion extending from the second end of the head to a third end along the central longitudinal axis, the connection portion including an oblong hole elongated in a direction parallel to the central longitudinal axis, and a shaft extending from the third end of the connection portion to a fourth end along the central longitudinal axis. The shaft includes third and fourth fixation element holes extending along the central longitudinal axis. The shaft includes a plurality of first projections and a plurality of second projections. The first and second projections include corresponding projection fixation element holes extending therethrough and being connected to the shaft. The first and second projections are alternatingly provided on the shaft.

20 Claims, 5 Drawing Sheets

LOCKING WEB PLATE

PRIORITY CLAIM

The present application is a Continuation application of U.S. patent application Ser. No. 14/320,511 filed on Jun. 30, 2014. The disclosure of the above patent(s)/application(s) is incorporated herein by reference.

FIELD OF THE INVENTION

The present invention generally relates to plates for the fixation of fractures in the hand and methods of implanting these plates on bone.

BACKGROUND

Current systems and methods for the fixation of certain fractures include bone plates which must be contoured by a surgeon to conform to the curvature of the bone. The surgeon uses forceps or another tool to grip the bone plate and manually manipulates the bone plate to achieve a curvature that approximates that of the bone. The rigidity of these bone plates renders them difficult to manipulate curve as desired and the construction of many conventional bone plates does not permit curvature in a multitude of planes to closely match the complex curvature of a target bone.

SUMMARY OF THE INVENTION

The present invention is directed to a bone plate sized and shaped for fixation to a phalanx, the bone plate comprising a head extending from a first end to a second end and having first and second fixation element holes extending therethrough along first and second fixation element hole axes. The bone plate also comprises a connection portion extending from the second end of the head to a third end along the central longitudinal axis, the connection portion including an oblong hole elongated in a direction parallel to the central longitudinal axis. The bone plate also comprises a shaft extending from the third end of the connection portion to a fourth end along the central longitudinal axis, the shaft including third and fourth fixation element holes extending along the central longitudinal axis, the shaft including a plurality of first projections extending along a first lateral wall and a plurality of second projections extending along a second lateral wall, the first and second projections including corresponding projection fixation element holes extending therethrough and being connected to the shaft by a reduced diameter extension, wherein the first and second projections are alternatingly provided on the shaft.

BRIEF DESCRIPTION OF THE DRAWINGS

Several embodiments of the invention will be described in the following by way of example and with reference to the accompanying drawings in which.

DETAILED DESCRIPTION

Figure 1:
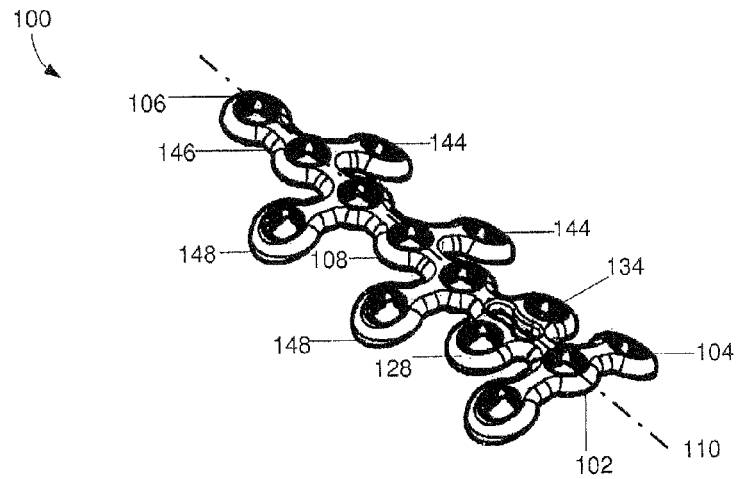
FIG. 1 shows a perspective view of a bone plate according to a first exemplary embodiment of the invention.

The present invention may be further understood with reference to the following description and the appended drawings, wherein like elements are referred to with the same reference numerals. The present invention relates to apparatus and methods for the treatment of fractures and, in particular, to devices for fixing fractures of the metacarpals. More specifically, the exemplary bone fixation plate according to the invention may be placed over a metaphyseal region of a bone to capture fragments within the head of the bone. Exemplary embodiments of the present invention describe a bone fixation plate having a head and an elongated shaft, which plate structured for positioning against an outer surface of a fractured or otherwise damaged bone. Portions of the bone plate surrounding a plurality of holes extending therethrough are connected to one another by webs which are less wide than the holes forming notches between the holes. As will be described in greater detail later on, the notched profile of the exemplary bone plate reduces the force required to bend the bone plate without compromising the structural integrity of the plate. The bone plate further comprises a connection region extending between the head and an elongated shaft thereof. The connection region includes one or more plate holes and an oblong through opening having a longitudinal axis extending substantially parallel to a longitudinal axis of the bone plate. In an exemplary embodiment, the oblong opening has rounded ends and a narrowed mid-section resembling a figure-8. As will be described in greater detail later on, this through opening is positioned and oriented to aid in shaping the bone plate to match a contour of the bone. The elongated shaft includes a first body portion extending parallel to the longitudinal axis of the bone plate and including a plurality of plate holes extending therethrough. The shaft further includes a second body portions extending out of first and second lateral walls thereof along second body portion axes angularly offset from the longitudinal axis of the bone plate. The second body portions include plate holes extending therethrough positioned such that the plate holes of the second body portion are axially offset from plate holes of the first body portion. The exemplary bone plate is pre-formed with a contour substantially matching a contour of a portion of a target bone on which the plate is to be mounted. It is noted that although the exemplary system and method are directed to fixation of fractures of the metacarpals, the exemplary bone fixation system may be used in any other bone without deviating from the scope of the invention. For example, the plate may be used for the fixation of bones of the feet such as the phalanxes and metacarpals.

Figure 2:
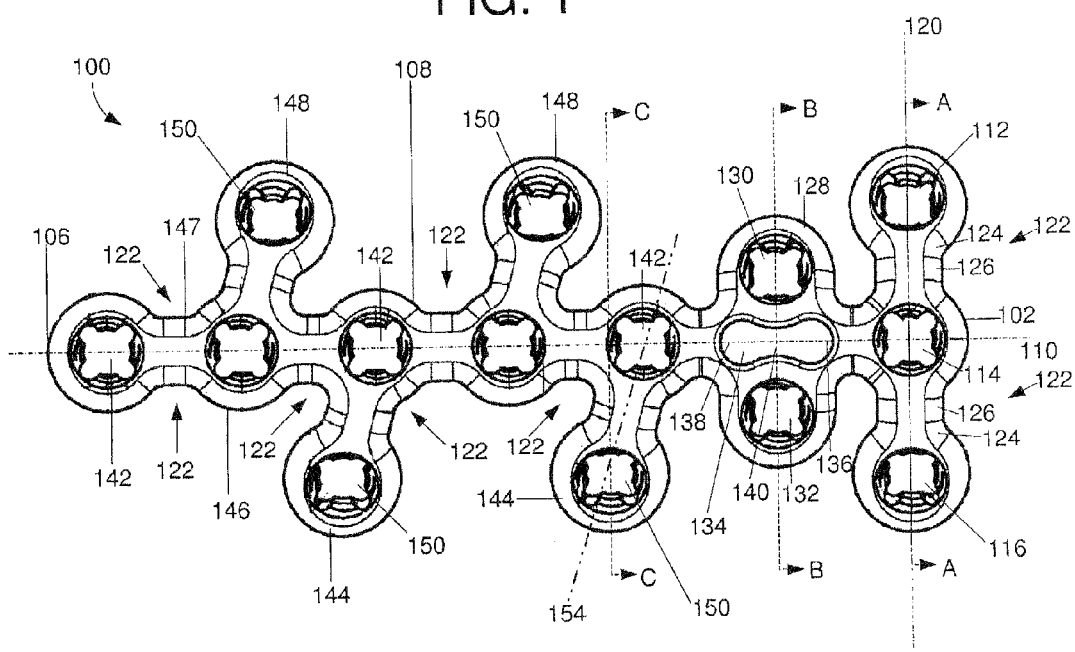
FIG. 2 shows a top view of the bone plate of FIG. 1.
Figure 3:
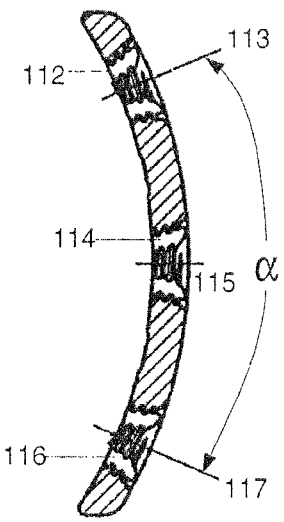
FIG. 3 shows a cross-sectional view of the bone plate of FIG. 1 taken along line A-A.

As shown in FIGS. 1-6, a bone plate 100 according to the present invention extends from a first end 102 including a head 104 to a second end 106 including a shaft 108 along a central longitudinal axis 110. The bone plate 100 includes a head 104 having a width greater than that of the shaft 108. Three variable angle holes 112, 114, 116 extend through the head 104 and are aligned with one another along an axis 120 extending orthogonal to the central longitudinal axis 110. In an exemplary embodiment, the head 104 has a first curvature, as shown in FIG. 3, selected to correspond to a curvature of a portion of bone on which the head 104 is to rest (which curvature may then be modified as desired by the surgeon to adapt the plate 100 to the specific anatomy of the bone being treated). The curvature of the head 104 in this exemplary embodiment is selected so that plate hole axes 113, 117 of the plate holes 112, 116, respectively, intersect at an angle α of 46°. The plate holes 112, 116 have been oriented to extend orthogonal or substantially orthogonal to the plane of the plate, accounting for the curvature thereof, as will be described in greater detail later on. This configuration is also selected to not reduce the number of thread turns in the plate holes 112, 116. Furthermore, this configuration ensures that tips of bone screws inserted in plate holes 112, 114, 116 do not encounter each other within the bone. In some embodiments, the angle α may be smaller than 46° and may be as small as 0°. A plate hole axis 115 of the plate hole 114 in this embodiment extends orthogonal to a top surface of the bone plate 100 bisecting the angle formed by the intersection of the axes 113 and 117. In an exemplary embodiment, the pre-formed curvature of the bone plate 100 is substantially uniform and symmetric about the central longitudinal axis 110. In another embodiment, the bone plate 100 may have an asymmetric curvature relative to the axis 110. In an alternative embodiment, a radius of the head 104 may have a radius of curvature that varies along the length of the head 104. A first web 122 extends between the portion of the head 104 surrounding the hole 112 and the portion of the head 104 surrounding the hole 114. A second web 122 extends between the portion of the head 104 surrounding the hole 114 and the portion of the head 104 surrounding the hole 116. The webs 122 form notches 124 between the larger diameter portions of the head 104 surrounding the holes 112, 114 and 116 reducing a profile of the head 104 while maintaining the structural integrity of the bone plate 100. In an exemplary embodiment, the notches 124 form a substantially concave cutout along the outer periphery of the head 104. A width of the webs 122 is preferably at least 2.4 mm±0.5 mm. In the present embodiment, the plate holes 112, 114, 116 are separated from one another by a distance permitting a portion 126 of each of the sides of the webs 122 to extend substantially straight at the minimum width of the web 122. It is noted that a length of the planar portion 126 may be altered to achieve a desired spacing between the plate holes 112, 114, 116 or to accommodate a greater number of plate holes while minimizing any increase in the width of the head 104.

Figure 4:
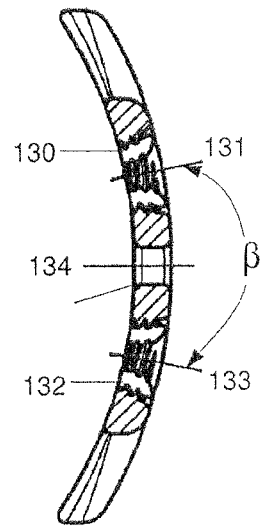
FIG. 4 shows a cross-sectional view of the bone plate of FIG. 1 taken along line B-B.

A connection region 128 extends between the shaft 108 and the head 104 and is formed with a width smaller than a width of the head 104 but greater than a width of the shaft 108. The shaft 108 includes a connection region 128 including a pair of variable angle holes 130, 132 extending therethrough. As shown in FIG. 4, a curvature of the connection region 128 according to this embodiment is selected such that plate hole axes 131, 133 of the holes 130, 132 intersect at an angle β of 23 degrees. Similar to the angle α, the angle β may be selected such that plate holes 130, 132 extend orthogonal or substantially orthogonal to the plane of the plate, accounting for the curvature thereof, as will be described in greater detail later on. Furthermore, this configuration ensures that tips of bone screws inserted in plate holes 130, 132 do not encounter each other within the bone. In some embodiments, the angle β may be smaller than 23° and may be as small as 0°. An oblong hole 134 extends through the connection region 128 with a longitudinal axis thereof aligned with the central longitudinal axis 110. The hole 134 has rounded ends which are wider than a middle region thereof so that the hole 134 resembles a figure-8. That is, the hole 134 comprises two substantially circular openings 136, 138, respectively, separated from one another along the longitudinal axis by a distance greater than the diameter of the openings 136, 138 and open to one another via a middle region 140 whose width is less than the diameter of the circular openings 136, 138, as shown in FIG. 2. This exemplary configuration facilitates bending of the head 104 and shaft 108 about the middle region 140 of the hole 134 as desired to more closely match the curvature of a target portion of a target bone.

Figure 5:
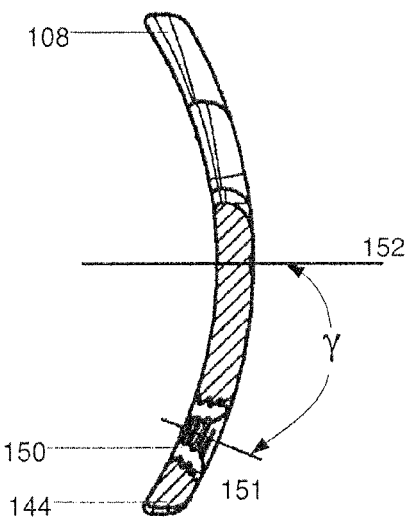
FIG. 5 shows a cross-sectional view of the bone plate of FIG. 1 taken along line C-C.
Figure 6:
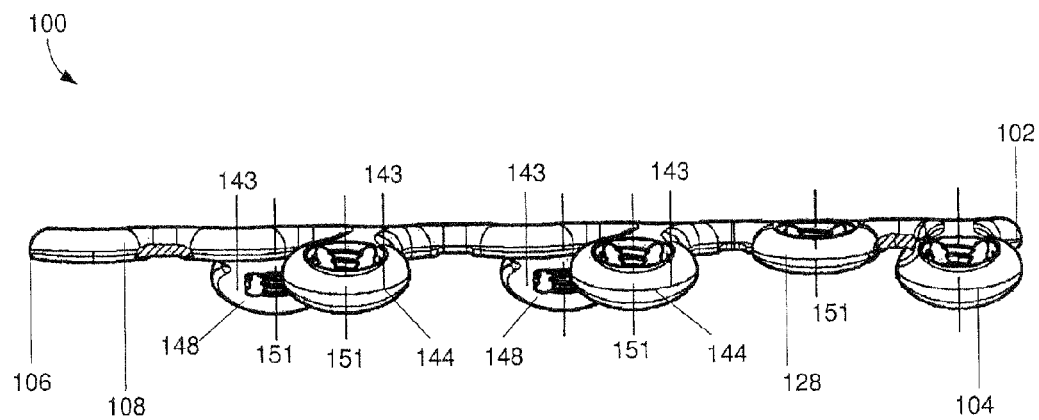
FIG. 6 shows a lateral view of the bone plate of FIG. 1.

The shaft 108 extends away from the connection region 128 along the central longitudinal axis 110. A plurality of variable angle plate holes 142 are formed through the shaft 108 along the central longitudinal axis 110. Plate hole axes 143 of the plate holes 142 in this embodiment are substantially orthogonal to a top surface of the bone plate 100. However, as those skilled in the art will understand, each of the plate hole axes 143 may be at any desired angle so that the range of angulation available via the corresponding variable angle hole 142 provides the range of angulation desired for that hole 142. A plurality of first projections 144 extend laterally outward from a first lateral wall 146 of the shaft 108 and a plurality of second projections 148 extend laterally outward from a second lateral wall 147. Each of the first and second projections 144, 148 includes a variable angle plate hole 150 extending therethrough. As shown more clearly in FIG. 5, the plate 100 is curved in the area of the first projection 144 so that a plate hole axis 151 of the plate hole 150 forms an angle γ with an axis 152 extending through the bone plate 100 and intersecting the central longitudinal axis 110 perpendicular to a surface of the plate 100. In an exemplary embodiment, a curvature of the shaft 108, as shown in FIG. 5, is different from a curvature of the head 104 to conform to the anatomy of the bone. Those skilled in the art will understand that the curvature of the plate 100 along the length of the shaft 108 may remain constant or vary as required to conform to the shape of the portion of bone over which the plate 100 is to be mounted. As shown in FIG. 1, the first projection 144 extends away from the central longitudinal axis 110 angled toward the second end 106. In a preferred embodiment, a longitudinal axis 154 of the first projection 144 forms an angle of approximately 22° with the central longitudinal axis. This angle is selected to ensure that a screw inserted in plate hole 150 may be positioned within the bone and may range between 10 and 90°, depending on the position of the hole 150 in the plate (e.g., depending on a distance between axis 110 and axis plate hole 150). The second projections 148 are substantially similar to the first projections 144 and include plate holes 150 extending therethrough. However, unlike the first projections 144, the second projections 148 extend away from the shaft 108 toward the first end 102. An angle enclosed by a longitudinal axis of the second projection 148 is the same as that of the first projection 144. In an alternate embodiment, an angle enclosed by the first projections 144 is not the same as the angle enclosed by the second projections 148. In an exemplary embodiment, the shaft 108 includes alternating ones of the first and second projections 144, 148, beginning with the first projection 144 to prevent screw collision of screws inserted through the first and second projections 144, 148. The exemplary layout of the first and second projections 144, 148 also helps to distribute stress across the bone and bone plate 100 and increases bony purchase of the bone screws on select portions of the bone not typically accessible via standard fixation plates. It is noted that although the exemplary embodiment is depicted with four projections, any number and placement thereof may be used to conform to the requirements of a particular procedure. The shaft 108 further includes a plurality of webs 122 connecting the portions of the plate 100 surrounding the plate holes 142 and the portions of the plate 100 connecting the projections 144, 148 to the shaft 108. As described in greater detail earlier, the webs 122 are sized to minimize an outer profile of the bone plate 100 while maintaining strength thereof. As shown in FIG. 1, an outer periphery of the bone plate 100 according to this embodiment includes a rounded taper to further reduce the profile.

In accordance with an exemplary method according to the invention, the head 104 is positioned over a metaphyseal region of a target bone with the shaft 108 extending toward the diaphysis of the bone, as those skilled in the art will understand. The head 104 of the bone plate 100 extends around a portion of the metaphyseal region to capture fracture fragments. If deemed necessary, the surgeon or other user may use a tool (e.g., pliers, forceps, etc.) to adapt the curve of the head 104, the shaft 108 and any or all of the first and second projections 144, 148 to provide flush seating of the bone plate 100 over the bone. As described in greater detail above, the exemplary construction of the bone plate 100 permits the bending of individual portions thereof in a plurality of planes and further permits the bending of particular portions of the bone plate (e.g., the first and second projections 144, 148) without affecting the curvature of adjacent portions of the bone plate 100. In contrast, prior art systems are not only cumbersome to bend due to their rigid profile but also prevent the independent curvature of select portions of the bone plate. Thus, the exemplary embodiment of the invention permits selective bending of the bone plate to match the curvature of the bone. Still further, the oblong hole 134 permits bending of the head 104 relative to the shaft 108 along the central longitudinal axis. Once the bone plate 100 has been bent to a desired curvature, the bone plate is positioned over and secured to the bone using bone screws (e.g., variable angle locking screws, not shown) inserted into the plate holes 112, 114, 116, 142, 130, 132 and 150 at any of the locations desired and in an order determined by the surgeon based on the properties of the fracture. All the plate holes 112, 114, 116, 130, 132, 142, 150 in the bone plate 100 according to this embodiment are 1.5 mm. locking compression plate screw holes formed to receive 1.5 mm cortex screws or 1.5 mm locking screws, as those skilled in the art will understand. It is noted, however, that any other size plate hole may be substituted for any or all of these holes without deviating from the scope of the invention. One such alternate size is described below with respect to FIGS. 7-8.

Figure 7:
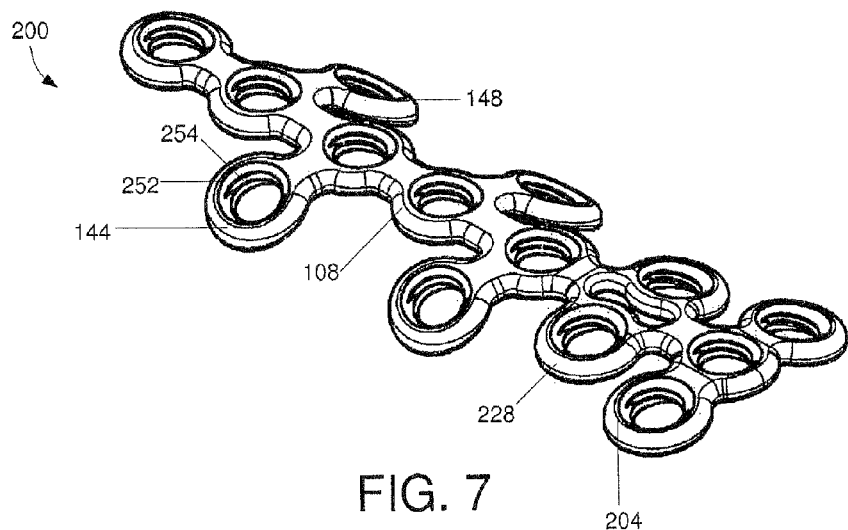
FIG. 7 shows a perspective view of a bone plate according to a second exemplary embodiment of the invention.
Figure 8:
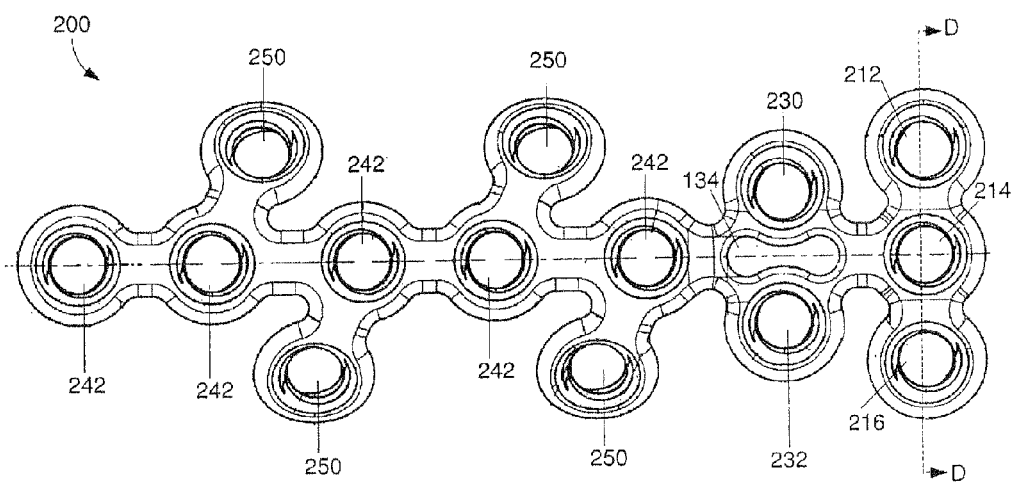
FIG. 8 shows a top view of the bone plate of FIG. 7.
Figure 9:
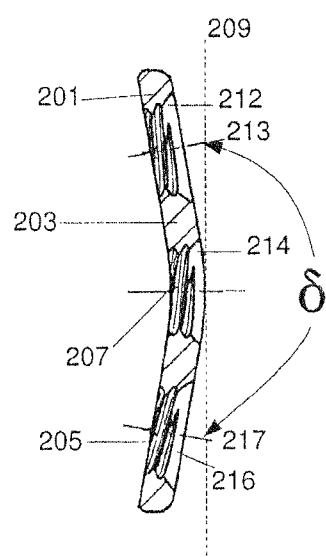
FIG. 9 shows a cross-sectional view of the bone plate of FIG. 7 taken along line D-D.

FIGS. 7-9 depict a bone plate 200 according to another embodiment of the invention. The bone plate 200 is formed substantially similarly to the bone plate 100 except as noted below. The bone plate 200 includes plate holes 212, 214, 216, 230, 232, 242, 250 corresponding to the plate holes 112, 114, 116, 130, 132, 142, 150 of the bone plate 100. However, the plate holes 212, 214, 216, 230, 232, 242, 250 are 1.3 mm plate holes. Furthermore, whereas the bone plate 100 is formed with a substantially rounded curvature, the bone plate 200 is preformed with a combination of planar bends and curvatures, as will be described in greater detail hereinafter.

As shown in FIG. 9, plate hole axes 213, 217 of the plate holes 212, 216 intersect at an angle δ of 20 degrees. It is noted that this angle is exemplary only and that other angles may be used without deviating from the scope of the invention such as, for example, the angles described above with respect to the bone plate 100. A bone-contacting surface 201 of the bone plate 200 is precontoured with a bend defining first and second planar walls 203, 205 which meet at either a pointed or substantially rounded junction 207. In an exemplary embodiment, the planar walls 203, 205 are bent approximately 10 degrees relative to an axis 209 corresponding to a planar, non-bent configuration of the bone plate 200. The exemplary planar walls 203, 205 provide a profile that is a better fit to the metaphysis of the phalanx and further facilitate the manufacturing process. When using 1.5 mm holes, the planar walls 203, 205 allow for a close match to an outer profile of a metacarpal metaphysis. A connection region 228 of the bone plate 200 may be bent in the same manner as the head 204. The shaft 108 of the bone plate 200 may be curved in the same manner disclosed above with respect to the bone plate 100.

Furthermore, as shown in FIG. 7, the bone plate 200 may include conically threaded locking holes in place of variable angle holes, the locking holes including a non-threaded recess having a curved wall 252 to seat a semi-circular head (not shown) of a bone screw (not shown) and a threaded shaft portion 254 with threads formed to threadedly engage a shaft of the bone screw.

It will be appreciated by those skilled in the art that various modifications and alterations of the invention can be made without departing from the broad scope of the appended claims. Some of these have been discussed above and others will be apparent to those skilled in the art.

What is claimed is:

1. A method for bone fixation, comprising:
provisionally positioning a bone plate over a phalanx, the bone plate including a head extending from a first end to a second end and having first and second fixation element holes extending therethrough along first and second fixation element hole axes, a connection portion extending from the second end of the head to a third end along the central longitudinal axis, the connection portion including an oblong hole elongated in a direction parallel to the central longitudinal axis, and at least one connection portion fixation element hole positioned laterally of the oblong hole and orthogonally to the central longitudinal axis; and a shaft extending from the third end of the connection portion to a fourth end along the central longitudinal axis, the shaft including third and fourth fixation element holes extending along the central longitudinal axis, the shaft including a plurality of first projections extending along a first lateral wall and a plurality of second projections extending along a second lateral wall, the first and second projections including corresponding projection fixation element holes extending therethrough, each of the first and second projections being connected to the shaft by a reduced diameter extension, wherein the reduced diameter extensions connect to the shaft at positions that alternate along the length of the shaft so that a first projection extends from a portion of the shaft between adjacent ones of the second projections;
bending the bone plate to conform to the anatomy of the phalanx, wherein the head is adjustable relative to the shaft about the oblong hole;
inserting a first fixation element into one of the first, second, third and fourth fixation element holes; and
inserting a second fixation element into a projection fixation element hole.

2. The method of claim 1, wherein each of the plurality of first and second projections is individually adjustable relative to the shaft.

3. The method of claim 1, wherein a fixation element is inserted into one of the first and second fixation element holes prior to the insertion of a fixation element into the third fixation element hole.

4. The method of claim 1, wherein an outer periphery of the bone plate includes a plurality of notches formed as indentations on an outer wall of the bone plate, the notches aiding in adjustment of the bone plate to conform to the anatomy of the phalanx.

5. The method of claim 4, wherein the notches are positioned between adjacent ones of the first, second, and third fixation element holes.

6. The method of claim 5, wherein the notches are positioned between adjacent ones of the plurality of shaft fixation element holes.

7. The method of claim 5, wherein the first, second and third fixation element holes and the shaft fixation element holes are variable angle holes.

8. The method of claim 1, wherein the head is formed with a first contour conforming to a curvature of a metaphysis of a metacarpal and the shaft is formed with a second contour conforming to a contour of a diaphysis of the metacarpal, wherein the first contour is different from the second contour.

9. A method for bone fixation, comprising:
provisionally positioning a bone plate over a target bone, the bone plate including a head extending from a first end to a second end and having first and second fixation element holes extending therethrough along first and second fixation element hole axes, a connection portion extending from the second end of the head to a third end along the central longitudinal axis, the connection portion including an oblong hole elongated in a direction parallel to the central longitudinal axis, and at least one connection portion fixation element hole positioned laterally of the oblong hole and orthogonally to the central longitudinal axis; and a shaft extending from the third end of the connection portion to a fourth end along the central longitudinal axis, the shaft including third and fourth fixation element holes extending along the central longitudinal axis, the shaft including a plurality of first projections extending along a first lateral wall and a plurality of second projections extending along a second lateral wall, the first and second projections including corresponding projection fixation element holes extending therethrough and being connected to the shaft by a reduced diameter extension, wherein the reduced diameter extensions connect to the shaft at positions that alternate along the length of the shaft so that a first projection extends from a portion of the shaft between adjacent ones of the second projections and wherein a cross-section of the oblong hole is a figure-eight;
bending the bone plate to conform to the curvature of the bone, wherein the head is adjustable relative to the shaft along the central longitudinal axis;
inserting a first fixation element into one of the first, second, third and fourth fixation element holes; and
inserting a second fixation element into a projection fixation element hole.

10. The method of claim 9, wherein the head is positioned over a metaphyseal region of the target bone.

11. The method of claim 10, wherein the head is formed with a first contour conforming to a curvature of the metaphyseal region of the target bone and the shaft is formed with a second contour conforming to a contour of a diaphysis of the target bone, wherein the first contour is different from the second contour.

12. The method of claim 11, wherein the contour forms a portion of an arc of a cylinder.

13. The method of claim 9, wherein a width of the head is greater than a width of the connection portion and the shaft.

14. The method of claim 9, wherein the first, second and third fixation element holes and the shaft fixation element holes are variable angle holes.

15. A method for bone fixation, comprising:
positioning a bone plate over a target bone, the bone plate including a head extending from a first end to a second end and having first and second fixation element holes extending therethrough along first and second fixation element hole axes, a connection portion extending from the second end of the head to a third end along the central longitudinal axis, the connection portion including an oblong hole elongated in a direction parallel to the central longitudinal axis, and at least one connection portion fixation element hole positioned laterally of the oblong hole and orthogonally to the central longitudinal axis; and a shaft extending from the third end of the connection portion to a fourth end along the central longitudinal axis, the shaft including third and fourth fixation element holes extending along the central longitudinal axis, the shaft including a plurality of first projections extending along a first lateral wall and a plurality of second projections extending along a second lateral wall, the first and second projections including corresponding projection fixation element holes extending therethrough and being connected to the shaft by a reduced diameter extension, wherein the reduced diameter extensions connect to the shaft at positions that alternate along the length of the shaft so that a first projection extends from a portion of the shaft between adjacent ones of the second projections wherein the first projections are angled toward the first end and the second projections are angled toward the second end;
bending the bone plate to conform to the curvature of the bone, wherein the head is adjustable relative to the shaft along the central longitudinal axis;
inserting a first fixation element into one of the first, second, third and fourth fixation element holes.

16. The method of claim 15, wherein the first angle is the same as the second angle.

17. The method of claim 16, wherein a fixation element is inserted into one of the first and second fixation element holes prior to the insertion of a fixation element into the third fixation element hole.

18. The method of claim 15, further comprising:
inserting a second fixation element into a projection fixation element hole.

19. The method of claim 15, wherein a longitudinal axis of the first projections forms a first angle with the central longitudinal axis and a longitudinal axis of the second projections forms a second angle with the central longitudinal axis.

20. The method of claim 15, wherein the first, second and third fixation element holes and the shaft fixation element holes are variable angle holes.

* * * * *

UNITED STATES PATENT AND TRADEMARK OFFICE
CERTIFICATE OF CORRECTION

PATENT NO. : 9,974,584 B2  
APPLICATION NO. : 15/711545  
DATED : May 22, 2018  
INVENTOR(S) : Hashmi et al.

Page 1 of 1

It is certified that error appears in the above-identified patent and that said Letters Patent is hereby corrected as shown below:

In the Claims

Claim 16, Column 8, Line 47:
"16. The method of claim 15, wherein the first angle is the" should read "19. The method of claim 16, wherein the first angle is the"

Claim 17, Column 8, Line 49:
"17. The method of claim 16, wherein a fixation element is" should read "17. The method of claim 15, wherein a fixation element is"

Claim 19, Column 8, Line 56:
"19. The method of claim 15, wherein a longitudinal axis" should read "16. The method of claim 15, wherein a longitudinal axis"

Signed and Sealed this
Twenty-eighth Day of May, 2019

Andrei Iancu
*Director of the United States Patent and Trademark Office*